United States Patent [19]

Liberda et al.

[11] 4,094,902
[45] June 13, 1978

[54] PROCESS FOR THE MANUFACTURE OF PHOSPHORIC ACID-TRIS-(DIMETHYLAMIDE)

[75] Inventors: Heinz Liberda; Hellmuth Spes; Alfred Trommet, all of Burghausen, Germany

[73] Assignee: Wacker-Chemie GmbH, Munich, Germany

[21] Appl. No.: 747,573

[22] Filed: Dec. 6, 1976

[30] Foreign Application Priority Data

Dec. 23, 1975 Germany .............................. 2558186

[51] Int. Cl.$^2$ ............................................... C07F 9/22
[52] U.S. Cl. .................................................. 260/551 P
[58] Field of Search ...................................... 260/551 P

[56] References Cited

U.S. PATENT DOCUMENTS

| | | | |
|---|---|---|---|
| 2,487,859 | 11/1949 | Dickey et al. | 260/551 P X |
| 2,662,095 | 12/1953 | Isham | 260/551 P |
| 2,752,392 | 6/1956 | Saul et al. | 260/551 P X |
| 2,756,252 | 7/1956 | McKinnis | 260/551 P X |
| 3,084,190 | 4/1963 | Miller et al. | 260/551 P |
| 3,991,110 | 11/1976 | Jennings, Jr. | 260/551 P |

FOREIGN PATENT DOCUMENTS

| | | | |
|---|---|---|---|
| 900,814 | 1/1954 | Germany. | |
| 772,178 | 4/1957 | United Kingdom | 260/551 P |

*Primary Examiner*—Robert V. Hines
*Assistant Examiner*—Thomas A. Waltz
*Attorney, Agent, or Firm*—Allison C. Collard

[57] ABSTRACT

Process for the manufacture of phosphoric acid-tris-(dimethylamide) (C) by reacting phosphorus oxychloride and dimethylamine in a molar ratio of 1 to at least 3, under anhydrous conditions and, optionally, under the application of pressure, which comprises carrying out the reaction in two separate process stages, wherein, in the first stage the phosphorus oxychloride and dimethylammonium chloride are heated in a molar ratio of approximately 1 : 1.5, and in the second stage dimethylamine is added to a mixture containing about 1.5 gram atoms of chlorine bonded to phosphorus and consisting of phosphoric acid dimethylamide-dichloride (A) and phosphoric acid-bis-(dimethylamide)-chloride (B) in which the proportion of (A) is not more than 50 mole %, or added to B alone, C is separated off at the end of the amine absorption and the formed dimethylammonium chloride is returned to the first stage. The compound C produced is a valuable polar solvent and reaction medium with catalytic properties which is being used increasingly as an intermediate product.

10 Claims, No Drawings

PROCESS FOR THE MANUFACTURE OF PHOSPHORIC ACID-TRIS-(DIMETHYLAMIDE)

The invention relates to a process for the manufacture of phosphoric acid-tris-(dimethylamide) called Compound C in the following) obtainable by reacting phosphorus oxychloride with 6 moles of dimethylamine in an inert solvent (cf. "Methoden der organischen Chemie", HoubenWeyl, Vol. 12/2, 4th edition, 1964, page 465). The desired compound, can, however, also be prepared from phosphoric acid-bis-(dimethylamide)-chloride (called Compound B in the following) and 2 moles of dimethylamine, likewise in an inert solvent (cf. loc.cit., page 468 and German Pat. No. 900,814). According to both methods, the desired phosphorus compound is produced together with solid dimethylammonium chloride which can be separated off only at considerable expense and has to be worked up again to recover the free amine.

It is furthermore known to decompose the dimethylammonium chloride, precipitated as by-product in the production of C from phosphorus oxychloride and dimethylamine in organic solvents, by the addition of aqueous alkali hydroxide solutions in order to avoid the need for separation of the same, which, presents difficulties both because of the finely particulate, voluminous nature, and because of low, but significant solubility in organic solvents of dimethylammonium chloride. If phosphorus oxychloride is reacted with little more than 3 moles of dimethylamine, strongly, concentrated alkali hydroxide solutions are necessary in addition, since otherwise the reaction only proceeds as far as the stage of Compound B (cf. loc.cit., page 467, and U.S. Pat. No. 2,752,392).

However, the use of concentrated alkali favors the formation of by-products, such as pyrophosphoric acid-tetrakis-(dimethyl-amide) or the corresponding derivative of triphosphoric acid, which on account of their toxicity must be removed from the aqueous phase by subsequent acid hydrolysis. If, on the other hand, phosphorus oxychloride is reacted with at least 6 moles of dimethylamine, although it is possible to use dilute alkali hydroxide solutions, extremely large quantities of alkali hydroxide are necessary to recover the amine and consequently also large quantities of the aqueous solution, so that an additional extraction of the large quantities of Compound C remaining in the aqueous phase is necessary (cf. U.S. Pat. No. 3,084,190).

Attempts have also been made, to avoid the possible side reactions by treating the reaction mixture with water instead of using aqueous alkali (see German Pat. No. 2,156,868), but in that case, too, the simultaneous use of an organic solvent is necessary, which, in the case of compound C, is limited to chloroform, since otherwise too much of the desired product remains dissolved in the aqueous phase.

Further, a general process for the production of phosphoric acid triamides of secondary amides is already known, according to which it should be possible to circumvent the recovery of the amine from the hydrochloride by heating to temperatures of 140°–200° C phosphorus oxychloride with secondary amines in a molar ratio of 1:3 in the presence of a high-boiling, organic solvent until the termination of hydrogen chloride evolution (cf. loc.cit., page 468, and German Pat. No. 1,005,963). By carrying out actual tests of our own it was discovered, however, that Compound C cannot be produced according to this process. This negative result is confirmed by the investigations of H. Normant in "Zeitschrift fur Angewandte Chemie", Vol. 79, page 1033, 1967, which prove that Compound C is attached by Bronsted acids, such as hydrogen chloride, when heat is applied, at least one dimethylamino group being replaced by chlorine.

Not one of the known processes is satisfactory, however, for being carried out on a large industrial scale, since in all cases large quantities of solvent have to be distilled, which involves considerable expenditure on apparatus. Furthermore, hitherto in every case, large quantities of alkali had to be used in order to decompose the by-product dimethylammonium chloride, either in situ or after separation, back into the free amine, as this is necessary for reasons of economy. The empirical equation summing up all processes described hitherto for the production of C is accordingly:

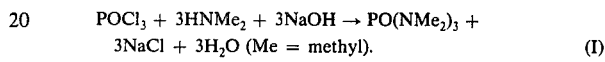

$$POCl_3 + 3HNMe_2 + 3NaOH \rightarrow PO(NMe_2)_3 + 3NaCl + 3H_2O \text{ (Me = methyl)}. \qquad (I)$$

It is the object of the invention to provide a process which renders possible the production of Compound C in good yields in a simple and economic manner without an auxiliary base, such as excess amine or aqueous alkali being necessary, so that in addition to Compound C the resulting hydrogen chloride can be recovered and pollution of the waste water can be avoided.

The process according to the invention for the manufacture of phosphoric acid tris-(dimethylamide) (C) by reacting phosphorus oxychloride and dimethylamine in a molar ratio of 1 to at least 3, under anhydrous conditions and optionally, under the application of pressure, is characterized by carrying out the reaction in two separate process stages; in the first stage the phosphorus oxychloride and dimethylammonium chloride are heated in a molar ratio of approximately 1:1.5 and in the second stage dimethylamine is added either to B alone or to a mixture containing approximately 1.5 gram atom of chlorine bonded to phosphorus said mixture consisting of phosphoric acid dimethylamidedichloride (A) and phosphoric acid-bis(dimethylamide)-chloride (B), in which the proportion of (A) is not more than 50 mole %, (C) is separated off at the end of the amine absorption, and the precipitated dimethylammonium chloride is returned to the first stage.

As mentioned before, the invention is based on the discovery that a division into 2 steps is necessary for making Compound C illustrated by the equation

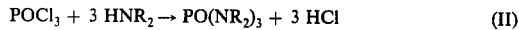

$$POCl_3 + 3 HNR_2 \rightarrow PO(NR_2)_3 + 3 HCl \qquad (II)$$

which cannot be carried out as a one-stage process without the addition of aqueous alkali (when R=methyl) on account of its tendency to split due to the hydrogen chloride formed.

In the first stage of the process phosphorus oxychloride, is heated, for example according to the process described in U.S. patent application Ser. No. 747,574 (filed concurrently under the internal reference Wa 7511), with a mixture of dimethylammonium chloride A and/or B to temperatures of 130°–240° C, wherein according to one embodiment of this process approximately 1.5 moles of dimethylammonium chloride is used per mole of phosphorus oxychloride.

The decisive feature for carrying out this process consists in that right at the beginning of the reaction at least one of the reactants A or B must be present. The initial ratio of the quantities of the two reactants A and B can vary within wide limits. The higher the proportion of A the more the reaction according to the equation $$POCl_2NMe_2 + (H_2NMe_2)^+Cl^- \rightarrow POCl(NMe_2)_2 + 2HCl \quad (III)$$

is favored which consumes the amine salt. When taking first pure A, it is advantageous to heat the mixture of A and amine salt for a short time to the reaction temperature, before adding phosphorus oxychloride, and then to introduce the phosphorus oxychloride slowly, i.e. in a proportion such as it is consumed by the formation of B for the reaction according to the equation $$POCl(NMe_2)_2 + POCl_3 \rightarrow 2POCl_2NMe_2 \quad (IV)$$

When taking first pure B, on the other hand, the phosphorus oxychloride can be introduced quickly without preheating the mixture of B and amine salt, since upwards of approximately 130° C it is consumed immediately by B, already present, for the reaction according to equation (IV).

When carrying out this process, it is, however, advantageous to use mixtures of A and B, mixtures of approximately equal parts by weight of A and B having proved particularly suitable. Under these conditions phosphorus oxychloride reacts with B to form A and the B thus consumed is continuously re-formed from A and amine salt. From the equations (III) and (IV) forming A and amine salt. From the equations (III) and (IV) forming the basis of these reactions there results, by addition, the equation $$2 POCl_3 + 3(H_2NMe_2)^+Cl^- \rightarrow POCl_2NMe_2 + POCl(NMe_2)_2 + 6HCl \quad (V)$$

This mixture, which under the conditions indicated consists of approximately equal molar portions of A and B, has then, in the second process stage, dimethylamine added to it, which reacts in a strongly exothermic reaction to form C in accordance with the following equation:

$$POCl_2NMe_2 + POCl(NMe_2)_2 + 6HNMe_2 \rightarrow 2PO(NMe_2)_3 + 3(H_2NMe_2)^+Cl^-, \quad (VI)$$

As is evident from (VI) at least 2 moles of dimethylamine are necessary per gram atom of chlorine bonded to phosphorus for the formation of C. So that in the second stage of the process on the one hand only C is produced and on the other hand as much amine salt is formed as is consumed in the first stage, there must be present in the intermediate products introduced into the second stage from the first stage altogether 1.5 gram atoms of chlorine bonded to phosphorus. This quantity of chlorine can, according to definition, be present either in the form of a mixture of A and B, in which the portion of A is not more than 50 mole %, or in the form of B alone, and can be ascertained, for example, by a determination of the chlorine content of the portions soluble in toluene or in another, non-polar, inert solvent. In the second stage we use therefore per gram atom of chlorine bonded to phosphorus, 2 to approximately 2.3 moles of dimethylamine, since a small excess does not interfere.

When carrying out the process according to the invention, advantageously dimethylamine is added to the mixture of approximately equal molar portions of A and B, obtained in the first process stage when the evolution of hydrogen chloride is practically complete, which mixture can, in some cases contain small quantities of unreacted dimethylammonium chloride. It is not absolutely necessary to change the reaction vessel. It is, however, advantageous to cool the mixture before adding the dimethylamine, since the reaction is strongly exothermic; without cooling to 50° C, the temperature might rise to the boiling point of the mixture (for example 240° C/760 mm Hg). Preferably the temperature is held at 80°–170° C, and in particular at 120°–170° C. The dimethylamine either can be introduced without solvent until complete saturation is reached, or can be introduced in the form of a solution in C. Once the addition of amine is complete, the reaction mixture is held at the temperature reached or desired until the amine is completely absorbed, i.e. until it no longer reacts. If desired, it is possible, by working in a closed system, to accelerate the amine absorption by means of the slight excess pressure produced as a result. It is, however, also possible to operate at slightly reduced pressure. From 120° C, the dimethylammonium chloride is practically completely dissolved in the reaction mixture, so that the reaction proceeds in homogeneous phase.

It is absolutely necessary to wait for the end of the amine absorption in order to ensure that no more B is present in the reaction mixture, which on account of having a similar boiling point to C cannot be separated by distillation.

Once the amine absorption is complete, the reaction mixture is advantageously cooled to approximately room temperature, the major part of the dimethylammonium chloride formed being crystallized out. Contrary to the known methods in inert, organic solvents, such as hydrocarbons or chlorinated hydrocarbons, the dimethylammonium chloride so obtained consists of large-grained particles, so that it can easily be removed by usual methods, such as centrifugation or filtration, and can be used again for the first process stage without further purification. Compound C is recovered from the filtrate by simple distillation.

According to a further embodiment of the process according to the invention, however, the separation of the dimethylammonium chloride is not necessary; it proved particularly advantageous to cool the reaction mixture at the end of the amine absorption to approximately 100° C and distill off the C formed under reduced pressure, directly from the reaction mixture. In the quantitative separation of Compound C the dimethylammonium chloride remains behind in the form of a porous solid which is used again for the first process stage without further purification.

However, in both methods it is not, absolutely necessary to separate the dimethylammonium chloride from Compound C or Compound C from the dimethylammonium chloride completely, since the latter can be reused for the first process stage without further purification. The quantities of C introduced into the first process stage in this manner are converted by the phosphorus oxychloride on heating by coproportioning into mixtures of A and B.

Considering the whole process, there are therefore practically no losses of yield of Compound C which, due to its good water-solubility, are usually unavoidable in the known processes, as a result of the treatment with dilute hydroxide solutions or water. Furthermore, owing to the division of the complete reaction into two process stages, the C formed is removed from the direct action of the hydrogen chloride formed in the first stage, which as a result of premature splitting, would otherwise render impossible the recovery of C without the addition of a base.

Without the separation of the dimethylammonium chloride formed in the second process stage, the entire process can also be carried out as a so-called "single vessel process" with the continuous succession of the two process stages, which is particularly economical. In this case, the mixture remaining after distilling off the major part of C, which mixture contains the dimethylammonium chloride and residual C, can in each case have phosphorus oxychloride added to it again and be heated to the temperature necessary for the first process stage. When the evolution of hydrogen chloride is practically complete, the dimethylamine is added.

If in the first process stage phosphorus oxychloride and dimethylammonium chloride are converted into A and B according to the process described in U.S. patent application Ser. No. 747,574 (concurrently filed under the internal reference Wa 7511), mixtures are obtained which altogether have more chlorine bonded to phosphorus than 1.5 gram atoms per mole of the phosphorus oxychloride used in the first stage. It is therefore necessary to use in the second process stage only a portion of the mixture corresponding to the desired quantity of chlorine and to retain the rest until the first process stage is repeated, when it is added, before the addition of phosphorus oxychloride, to the amine salt remaining after the second stage which may still contain some C.

When the two reactions succeed one another in the same vessel, excess of P-Cl compounds present after carrying out the first stage according to the process described in U.S. patent application Ser. No. 747,574, (filed concurrently under the internal reference Wa 7511) can be removed also by distillation, wherein predominantly the more readily boiling A is removed and B is concentrated. 1.5 gram atoms of chlorine bonded to phosphorus, in the form of B, yield in the reaction with at least 3 moles of dimethylamine, 1.5 mole of C, which corresponds to more gram atoms of phosphorus than have been introduced into the first stage in the form of phosphorus oxychloride. In this method of concentration of B it is therefore advantageous not to remove the total quantity of C at the end of the second process stage. The C remaining with the amine salt is, before the addition of the phosphorus oxychloride for the next repetition of the first stage, combined again with the distilled portion of the mixture from the preceding first stage and on heating with A, changes to B. This method of operation of the "single vessel process" has the additional advantage that C does not, after the second stage, have to be distilled off completely from the solid which crystallizes out.

The process according to the invention is distinguished, particularly from the commercial point of view, from the hitherto known processes by its economy and the fact that it is harmless to the environment, for it renders it possible to make economies by saving alkali as auxiliary and saving apparatus for separating, dissolving and working up the dimethylamine hydrochloride, and avoids the waste liquors resulting from the amine recovery. According to the new process it is possible to work also without solvent thereby omitting distillation and intermediate storage of the solvent and emission of solvent vapours.

The Compound C produced according to the process of the invention is a valuable, polar, aprotic solvent and reaction medium with catalytic properties which is being used increasingly as an intermediate product.

The process of the invention will be more fully described in the following examples which are given by way of illustration and not of limitation.

EXAMPLE 1

1 mole of phosphorus oxychloride (153.3 grams) and 1.5 mole of anhydrous dimethylammonium chloride (122.3 grams) were heated under reflux in a mixture of 162 grams of phosphoric acid-dimethylamide-dichloride (1 mole) and 170.5 grams of phosphoric acid-bis-(dimethylamide)-chloride (1 mole) until the evolution of HCl was complete. Of the resulting solution, 200 ml were distilled off at 12 mm Hg up to 110° C head temperature. This distillate contained 3.13 gram atoms of chlorine. 9 ml thereof were returned to the reaction vessel. The mixture was then saturated while stirring at, ultimately 140°–150° C, by the introduction of anhydrous dimethylamine through an inlet pipe extending into the gas space. Of the suspension obtained, approximately 200 ml of phosphoric-acid-tris-(dimethylamide) were distilled off at 1 mm Hg and 75–80%, of which the quantity exceeding 1 mole of phosphoric acid-tris-(dimethylamide) (179 grams) was returned to the reaction vessel including distillate obtained at 12 mm Hg. After heating to 150° C, addition of 1.0 mole of phosphorus oxychloride and heating under reflux until the HCl evolution was complete, 492 grams of a mixture having a composition (GC) of 47.1% phosphoric acid-dimethylamide-dichloride and 52.9% phosphoric acid-bis-(dimethylamide) chloride were obtained.

In the following examples 2 and 3, stage 2 is described first, and the reaction of $POCl_3$ with the amine salt follows as a separate stage, which is stage one Example 1 (in its present form).

EXAMPLE 2

A solution of 140 grams of dimethylamine (3.09 moles) in 400 grams of phosphoric acid tris-(dimethylamide) were added while stirring in a closed apparatus, to a mixture of 81 grams of phosphoric acid dimethylamide dichloride (0.5 mole) and 85.3 grams of phosphoric acid-bis-(dimethylamide)- chloride (0.5 mole). After the amine addition, the mixture was maintained at 80° C for half an hour, then cooled to room temperature and the dimethylammonium chloride which crystallized out was filtered off by suction. Of the filtrate, 400 grams were removed for the absorption of the quantity of amine for the following mixture, and the rest was purified by distillation under reduced pressure (5 mm Hg). 159 grams of phosphoric acid-tris-(dimethylamide) having a purity of 99.7% were obtained. The amine salt and distillation residue were reacted in double the quantity by weight of an approximately equimolar mixture of phosphoric acid-dimethylamide-dichloride and -bis-(dimethylamide)-chloride, with 153.3 grams of phosphorus oxychloride (1 mole) until the evolution of hydrogen chloride was practically complete.

EXAMPLE 3

Gaseous dimethylamine was introduced until saturation was obtained into a mixture of 0.5 mole each of phosphoric acid-dimethylamide-dichloride and -bis-(dimethylamide)-chloride, while stirring and with the exclusion of moisture, the temperature being maintained at 160° C. Subsequently the mixture was cooled to approximately 100° C and distilled under a vacuum of ultimately 1 mm Hg. 168 grams of phosphoric acid-tris-(dimethyl-amide) having a purity of 98.8% were The residue was reacted in the same reaction vessel with 1 mole of phosphorus oxychloride to form a mixture of phosphoric acid dimethylamide-dichloride and -bis-(dimethylamide)-chloride.

What is claimed is:

1. A process for the manufacture of phosphoric acid-tris-(dimethylamide), which comprises two stages carried out in repeated succession, wherein the first stage comprises reacting phosphorus oxychloride, dimethylammonium chloride, in an average amount of approximately 1.5 moles per mole of phosphorus oxychloride, and a member of the group consisting of phosphoric dimethylamide dichloride, phosphoric bis-dimethylamide chloride, and a mixture thereof, under anhydrous conditions and at a temperature within the range of from 130°–240° C, to give a mixture consisting of phosphoric bis-dimethylamide chloride and phosphoric dimethylamide dichloride; and wherein a second stage comprises reacting at least a portion of said last-mentioned mixture containing on average approximately 1.5 gram-atoms of phosphorus-bonded chlorine per mole of phosphorus oxychloride used in the first stage and containing not more than 50 mole % of phosphoric dimethylamide dichloride, with dimethylamine in an average amount of approximately 3 moles per mole of phosphorus oxychloride used in the first stage, under anhydrous conditions; and wherein, after completion of the reaction of the second stage, the phosphoric acid tris-(dimethylamide) produced in the second stage is separated off and the dimethylammonium chloride produced in the second stage is returned to the first stage.

2. The process for the manufacture of phosphoric tris-(dimethylamide), as claimed in claim 1, wherein the first stage is carried out at a temperature within the range of from 160° to 240° C.

3. The process as claimed in claim 1, wherein, in the first stage, the phosphoric dimethylamide dichloride and the phosphoric bisdimethylamide chloride are used in approximately equal amounts by weight.

4. The process as claimed in claim 1, wherein, at the end of the first stage, at least some of the phosphoric dimethylamide dichloride is distilled off and, in the second stage, predominantly phosphoric bisdimethylamide chloride is reacted with the dimethylamine.

5. The process as claimed in claim 1, wherein, in the second stage, the dimethylamine is used in an amount within the range of from 2 to 2.3 moles per gram-atom of phosphorus-bonded chlorine in the phosphoric dimethylamide dichloride and phosphoric bisdimethylamide chloride.

6. The process as claimed in 1, wherein, in the second stage, the dimethylamine is added to the other reactants in the absence of a solvent until saturation is reached and the temperature of the reactants is maintained at from 120° to 170° C.

7. The process as claimed in claim 1, wherein, the second stage, dimethylamine is added in the form of a solution in phosphoric tris-(dimethylamide), and the temperature is maintained at from 80° to 170° C.

8. The process as claimed in claim 1, wherein, after completion of the reaction of the second stage, the phosphoric tris-(dimethylamide) is distilled off from the dimethylammonium chloride.

9. The process as claimed in claim 1, wherein the dimethylammonium chloride returned from the second stage to the first stage contains some residual phosphoric tris-(dimethylamide).

10. The process as claimed in claim 1, wherein both stages of the process are carried out in the same vessel.

* * * * *

UNITED STATES PATENT OFFICE
CERTIFICATE OF CORRECTION

Patent No. 4,094,902            Dated June 13, 1978

Inventor(s) HEINZ LIBERDA ET AL

It is certified that error appears in the above-identified patent and that said Letters Patent are hereby corrected as shown below:

Column 1, line 59, delete "amides" and substitute therefor --amines--. Column 2, line 4, delete "attached" and substitute therefor--attacked--. Column 3, lines 31 and 32, delete "From the equations (III) and (IV) forming A and amine salt.". Column 6, line 25, delete "%" and substitute therefor--°C--. Column 7, line 4, after "were" insert --obtained--.

Signed and Sealed this

Twentieth Day of February 1979

[SEAL]

Attest:

RUTH C. MASON  
*Attesting Officer*

DONALD W. BANNER  
*Commissioner of Patents and Trademarks*